US012622596B2

(12) United States Patent     (10) Patent No.:   US 12,622,596 B2

Kodama et al.            (45) Date of Patent:     May 12, 2026

(54) IN-BODY MEASUREMENT SYSTEM, IN-BODY MEASUREMENT PROGRAM, AND COMPUTER-READALE NON-TRANSITORY STORAGE MEDIUM

(71) Applicant: TANITA CORPORATION, Tokyo (JP)

(72) Inventors: Miyuki Kodama, Tokyo (JP); Yasuhiro Kasahara, Tokyo (JP); Senri Tanida, Tokyo (JP)

(73) Assignee: TANITA CORPORATION, Tokyo (JP)

( * ) Notice: Subject to any disclaimer, the term of this patent is extended or adjusted under 35 U.S.C. 154(b) by 1141 days.

(21) Appl. No.: 17/463,683

(22) Filed: Sep. 1, 2021

(65) Prior Publication Data

US 2021/0393158 A1     Dec. 23, 2021

Related U.S. Application Data

(63) Continuation of application No. PCT/JP2020/009026, filed on Mar. 4, 2020.

(30) Foreign Application Priority Data

Mar. 6, 2019   (JP) ................................. 2019-040713

(51) Int. Cl.
    *A61B 5/0537*       (2021.01)
    *A61B 5/00*         (2006.01)
          (Continued)

(52) U.S. Cl.
    CPC .......... *A61B 5/0537* (2013.01); *A61B 5/4869* (2013.01); *A61B 5/4872* (2013.01);
          (Continued)

(58) Field of Classification Search
    None
    See application file for complete search history.

(56) References Cited

U.S. PATENT DOCUMENTS 4,895,163 A    1/1990   Libke et al.
2005/0222516 A1   10/2005   Kasahara et al.
           (Continued)

FOREIGN PATENT DOCUMENTS

CN     102355855 A    2/2012
CN     108618754 A    10/2018
           (Continued)

OTHER PUBLICATIONS

Chinese Office Action issued in Chinese Patent Application No. 202080018564.1 dated Oct. 1, 2024.

(Continued)

*Primary Examiner* — Michael R Bloch
(74) *Attorney, Agent, or Firm* — MCDONALD HOPKINS LLC

(57) ABSTRACT

A simplified BIA body composition analyzer (100) as an in-body measurement system, comprising: a memory unit (110) storing in-body information obtained by a measurement with a first precision as a reference value; a low-precision measurement unit (10) obtaining low-precision in-body information by inputting a measured value obtained by a measurement with a second precision that is lower than the first precision into a predetermined algorithm; a correction unit (112) correcting the algorithm or the low-precision in-body information based on the reference values stored in the memory unit (110) and the degree of importance placed on the reference values; and an output unit (106) outputting the low-precision in-body information obtained by the low-precision measurement unit (104) using the algorithm corrected by the correction unit (112), or the low-precision in-body information obtained by the low-precision measurement unit (104) and corrected by the correction unit (112), as corrected in-body information.

14 Claims, 9 Drawing Sheets

(51) Int. Cl.

| | | |
|---|---|---|
| *G01G 19/44* | (2006.01) | |
| *G16H 10/60* | (2018.01) | |
| *G16H 50/20* | (2018.01) | |
| *G16H 50/30* | (2018.01) | |

(52) U.S. Cl.
CPC .......... *A61B 5/4875* (2013.01); *A61B 5/7221* (2013.01); *A61B 5/7264* (2013.01); *A61B 5/742* (2013.01); *G01G 19/44* (2013.01); *G16H 10/60* (2018.01); *G16H 50/20* (2018.01); *G16H 50/30* (2018.01)

(56) References Cited

U.S. PATENT DOCUMENTS

| | | | | |
|---|---|---|---|---|
| 2007/0038140 | A1* | 2/2007 | Masuo | A61B 5/4869 |
| | | | | 600/547 |
| 2010/0081960 | A1* | 4/2010 | McKenna | A61B 5/4869 |
| | | | | 600/547 |
| 2010/0331629 | A1 | 12/2010 | Sato et al. | |
| 2012/0004570 | A1* | 1/2012 | Shimizu | A61B 5/055 |
| | | | | 600/587 |

| | | | | |
|---|---|---|---|---|
| 2013/0172776 | A1* | 7/2013 | Gaw | A61B 5/4878 |
| | | | | 600/547 |
| 2018/0263541 | A1 | 9/2018 | Kodama et al. | |

FOREIGN PATENT DOCUMENTS

| | | | |
|---|---|---|---|
| JP | H02-060626 | A | 3/1990 |
| JP | 2004-337578 | A | 12/2004 |
| JP | 2005-118149 | A | 5/2005 |
| JP | 2005-288023 | A | 10/2005 |
| JP | 2009-219742 | A | 10/2009 |
| JP | 2013-116258 | A | 6/2013 |
| JP | 2014-012083 | A | 1/2014 |
| WO | 2005/051194 | A1 | 6/2005 |
| WO | 2010/095709 | A1 | 8/2010 |

OTHER PUBLICATIONS

International Search Report issued in Patent Application No. PCT/JP2020/009026 dated May 26, 2020.

Japanese Office Action issued in Japanese Patent Application No. 2023-196296 dated Jun. 18, 2024.

Japanese Office Action issued in Japanese Patent Application No. 2025-076002 dated Oct. 21, 2025.

* cited by examiner

100

(a)

(b)

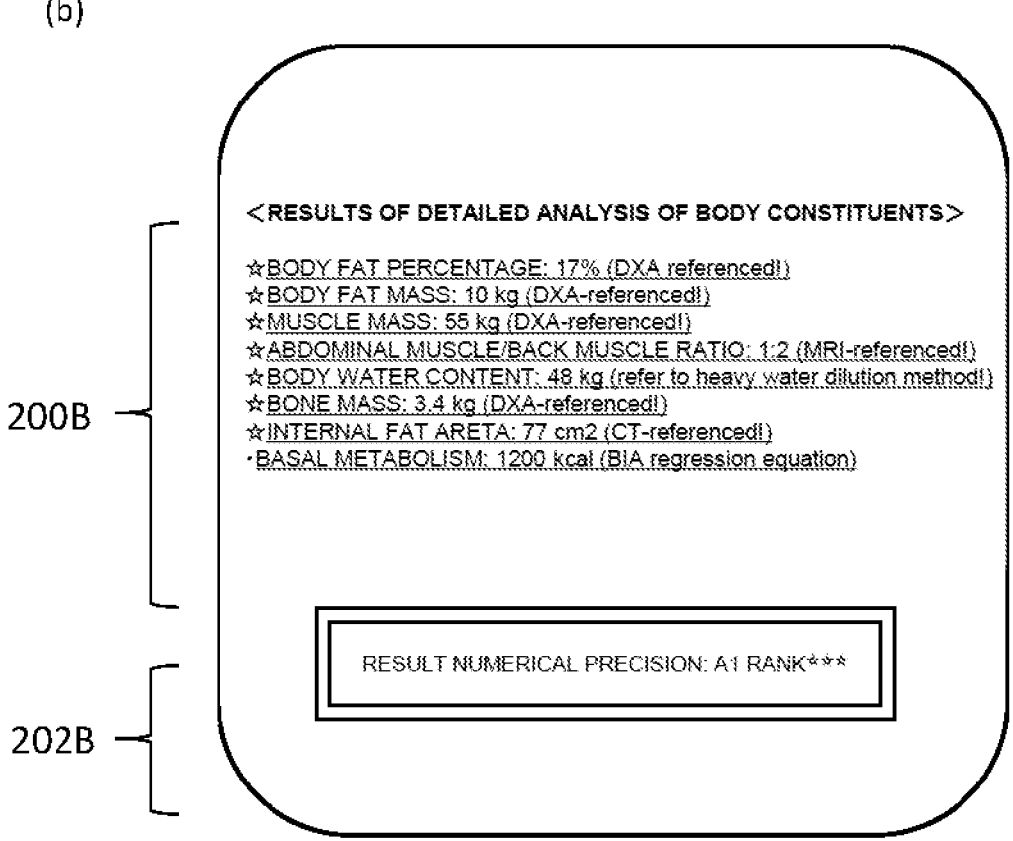

200B

202B

<RESULTS OF DETAILED ANALYSIS OF BODY CONSTITUENTS>

☆BODY FAT PERCENTAGE: 17% (DXA referenced!)
☆BODY FAT MASS: 10 kg (DXA-referenced!)
☆MUSCLE MASS: 55 kg (DXA-referenced!)
☆ABDOMINAL MUSCLE/BACK MUSCLE RATIO: 1:2 (MRI-referenced!)
☆BODY WATER CONTENT: 48 kg (refer to heavy water dilution method!)
☆BONE MASS: 3.4 kg (DXA-referenced!)
☆INTERNAL FAT ARETA: 77 cm2 (CT-referenced!)
·BASAL METABOLISM: 1200 kcal (BIA regression equation)

RESULT NUMERICAL PRECISION: A1 RANK***

Fig.5B

IN-BODY MEASUREMENT SYSTEM, IN-BODY MEASUREMENT PROGRAM, AND COMPUTER-READALE NON-TRANSITORY STORAGE MEDIUM

CROSS-REFERENCE TO RELATED APPLICATIONS

This application claims the benefit of Patent Application No. 2019-040713 filed in Japan on Mar. 6, 2019, the contents of which application are hereby incorporated by reference.

TECHNICAL FIELD

The present disclosure relates to an in-body measurement system, an in-body measurement program, and a computer-readable non-transitory storage medium.

BACKGROUND TECHNOLOGY

Conventionally, BIA body composition analyzers have been known to measure in-body information such as body water content, body fat content, and muscle mass based on the Bioelectrical Impedance Analysis (BIA) method. The BIA body composition analyzer is excellent in tracking the relative changes in-body information of individuals because it calculates the in-body information that applies to many people using a statistical formula.

U.S. Pat. No. 4,895,163 (Patent Document 1) and JP Patent Publication No. H2-60626 (Patent Document 2) propose a method of measuring the amount of fat in the body by measuring the impedance between the ends of the body and calculating the amount of fat in the body based on the values of the impedance and the body-related values such as the height, weight, and gender of the specimen.

SUMMARY

The absolute values of the in-body information obtained by conventional BIA body composition analyzers may differ slightly when compared to the in-body information obtained by high-precision measurement methods such as DXA (Dual Energy X-Ray Absorptiometry), MRI (Magnetic Resonance Imaging), CT (Computed Tomography), heavy water dilution method, and 4C model (four-compartment model).

In addition, among the BIA body composition analyzers, when the in-body information obtained by a simplified BIA body composition analyzer (e.g., single-frequency four-electrode BIA body composition analyzer, whole-body method BIA body composition analyzer) is compared with the in-body information obtained by a high-precision BIA body composition analyzer (e.g., multi-frequency and multi-electrode BIA body composition analyzer, site-specific BIA body composition analyzer), which has a higher measurement precision of the in-body information than the simplified BIA body composition analyzer, there may be some differences in the absolute values.

It is an object of the present disclosure to provide an in-body measurement system and a program for obtaining high-precision in-body information.

To achieve the above-described object, one type of in-body measurement system comprises: a memory unit configured to store in-body information obtained by a measurement with a first precision as a reference value; a low-precision measurement unit configured to obtain low-precision in-body information by inputting a measured value obtained by a measurement of a second precision that is lower than the first precision into a predetermined algorithm; a correction unit configured to correct the algorithm or the low-precision in-body information based on the reference values stored in the memory unit and the degree of importance placed on the reference values; and an output unit configured to output the low-precision in-body information obtained by the low-precision measurement unit using the algorithm corrected by the correction unit, or the low-precision in-body information obtained by the low-precision measurement unit and corrected by the correction unit, as corrected in-body information.

With this configuration, corrected in-body information is obtained by inputting measurement value obtained by a measurement with the second precision measurement (hereinafter also referred to as "low-precision"), which is lower than the first precision (hereinafter also referred to as "high-precision"), into an algorithm that has been corrected using the reference values obtained from the measurement with the first precision. Alternatively, corrected in-body information can be obtained by correcting the user's low-precision in-body information obtained by the low-precision measurement unit using high-precision reference values. In this case, as the high-precision reference value for obtaining corrected in-body information, in-body information obtained by the measurement with high-precision is not used as they are, but rather in-body information that has been adjusted using the degree of emphasis placed on the high-precision reference values (hereinafter also referred to as "adjustment parameter") is used. Therefore, a more appropriate high-precision reference value can be used for correction, and high-precision in-body information can be obtained as corrected in-body information. The adjustment parameter, for example, may be determined as necessary according to the possibility or degree of difference in body composition between the time (hereinafter also referred to as "low-precision measurement time") of measuring low-precision in-body information (hereinafter also referred to as "low-precision reference value") for determining correction methods by adjusting the high-precision reference value and the high-precision measurement time, or the high-precision reference values may not be adjusted.

The degree may be determined in accordance with the contribution of the reference value stored in the memory unit to the low-precision in-body information obtained by the low-precision measurement unit.

This configuration allows the degree to be determined in consideration of the contribution of the low-precision in-body information to the reference value.

The degree may be determined based on difference between body weight when the measurement with the first precision is performed and body weight when the measurement with the second precision is performed.

This configuration allows the possibility or degree of differences in body composition between the high-precision measurement time and the low-precision measurement time to be determined by the difference in body weight.

The degree may be determined based on a period of time between performing the measurement with the first precision and performing the measurement with the second precision.

This configuration allows the possibility or degree of differences in body composition between the high-precision measurement time and the low-precision measurement time to be determined based on the time period from the high-precision measurement time to the low-precision measurement time.

The degree may be determined further based on the difference between the reference value and the low-precision in-body information obtained by the low-precision measurement unit.

This configuration allows the possibility or degree of differences in body composition between the high-precision measurement time and the low-precision measurement time to be determined based on the difference between the low-precision in-body information as the low-precision reference value and the reference value.

The degree may be determined based on the user's choice.

This configuration allows the degree to be determined based on the user's selection.

The memory unit may be configured to store the corrected algorithm or the correction function for correcting the low-precision in-body information and the corrected in-body information.

With this configuration, the corrected algorithm or the correction function and the corrected in-body information are stored, so that they can be referred to later.

The system may further comprise an input unit configured to input the in-body information obtained in the measurement with first precision as the reference value by receiving the in-body information.

With this configuration, the reference value can be input simply.

The output unit may be configured to display the corrected in-body information and the low-precision in-body information obtained by the low-precision measurement unit in a distinguishable appearance.

This configuration allows the user to know whether the in-body information has been made with high-precision or not.

The output unit may be configured to display information related to the precision of the corrected in-body information based on the degree.

This configuration allows the user to know how highly precise the measurement result is corrected.

The output unit may be configured to display an alert based on a period of time between the measurement with the first precision and the measurement with the second precision.

This configuration can encourage the user to take a new high-precision measurement and motivate to increase the precision of the body measurement system.

To achieve the above-described object, one type of in-body measurement system causes a computer to function as the memory unit, the low-precision measurement unit, the correction unit, the output unit, and the input unit comprising the above-mentioned in-body measurement system.

BRIEF DESCRIPTION OF THE DRAWINGS

FIG. 5B shows a second result display screen of the simplified BIA body composition analyzer according to the first embodiment;

DESCRIPTION OF THE EMBODIMENTS

The embodiments of the present disclosure are described below with reference to the drawings. The embodiments described below are examples of how the present disclosure may be implemented, and do not limit the present disclosure to the specific configurations described below. In the implementation of the present disclosure, specific configurations may be adopted as appropriate according to the form of implementation.

(Configuration of a Body Composition Analyzer)

Figure 1:
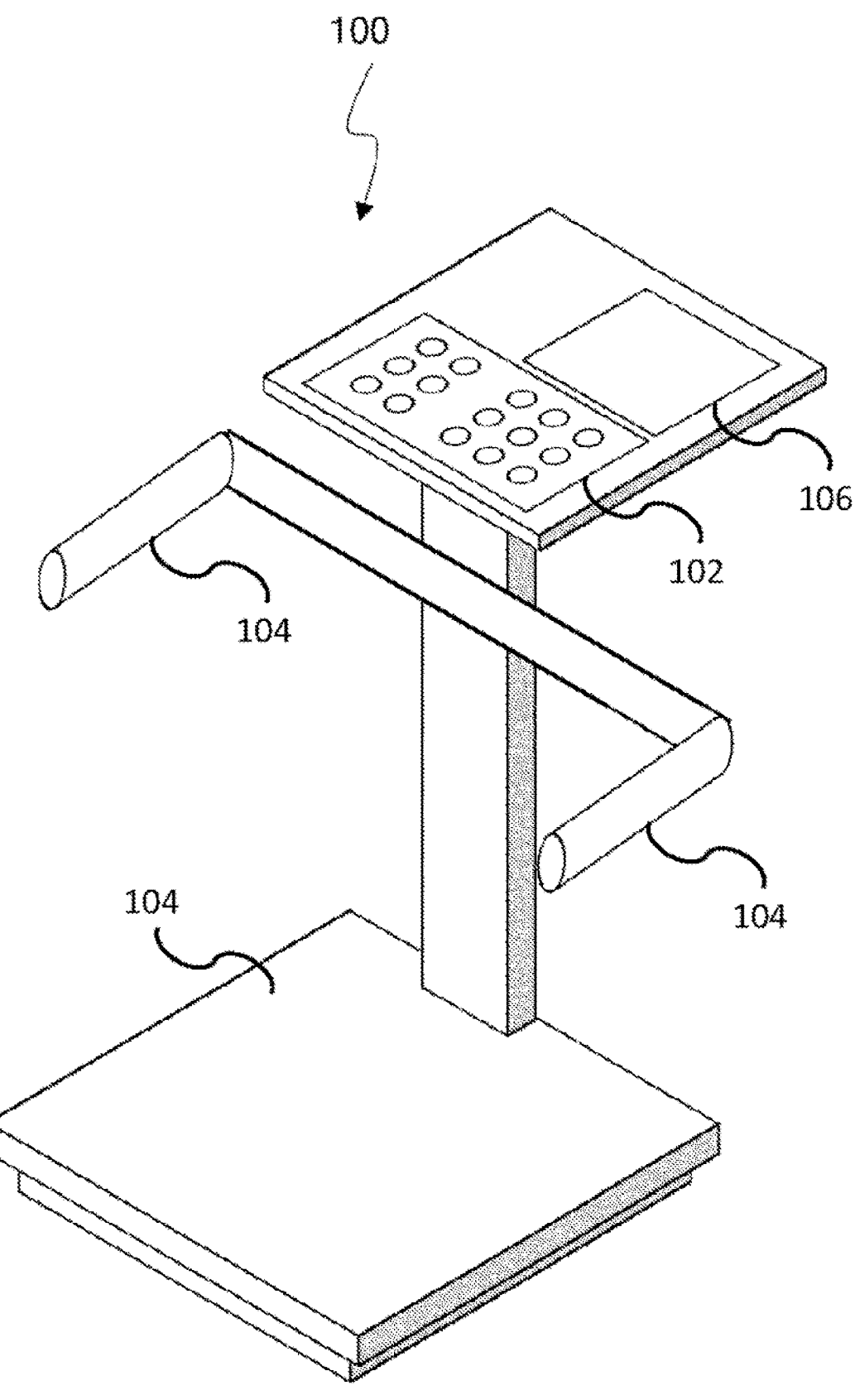
FIG. 1 shows a diagram of a simplified BIA body composition analyzer according to an embodiment.

FIG. 1 is a diagram of a simplified BIA body composition analyzer 100 according to an embodiment of the present disclosure. The simplified BIA body composition analyzer 100 has an input unit 102, a low-precision measurement unit 104, and an output unit 106.

The input unit 102 is a means of inputting information to the simplified BIA body composition analyzer 100. The method of inputting information by the input unit 102 may be a manual method, a method via a recording medium, a method via wired communication, a method via wireless communication, or any other method.

The manual input method may be, for example, a button type, a dial type, or a touch sensor type. The method via a recording medium may be, for example, a flash memory method, a CD-ROM method, or a DVD-ROM method. The method via wireless communication may be, for example, a method via the Internet, a method via a wireless LAN such as Wi-Fi (registered trademark), or a method via short-range wireless communication such as Bluetooth (registered trademark) or NFC (Near Field Communication). In the present embodiment, the input unit 102 is a manual input method and is a button type.

Information related to body composition is input to the input unit 102. Specifically, information that cannot be measured by the simplified BIA body composition analyzer 100, such as, for example, age, height, and gender, is input to the input unit 102.

In addition, the input unit 102 further inputs high-precision in-body information, among in-body information such as body fat percentage, body fat mass, muscle mass, abdominal/back muscle ratio, body water content, bone mass, visceral fat area, basal metabolism, and so on, which is measured by a body composition measurement (estimation) method (for example, DXA, MRI, CT, heavy water dilution method, 4C model) or a high-precision BIA body composition analyzer (multi-frequency and multi-electrode BIA body composition analyzer, site-specific BIA body composition analyzer), which has a higher measurement precision of in-body information compared to a simplified BIA body composition analyzer.

In addition, the weight and the date and time of measurement when the high-precision in-body information is measured are also input to the input unit 102.

The inputted information is stored in a memory unit 110, which will be described later.

The low-precision measurement unit 104 is a measurement means for measuring low-precision in-body information of a user by inputting measured values into a predetermined algorithm. The measured values are, for example, body weight, bioelectrical impedance, and the like. The predetermined algorithm may be, for example, a regression equation for calculating the low-precision in-body information from the measured values, or a machine learning model that outputs the low-precision in-body information using the measured values as input. In this embodiment, the low-precision measurement unit 104 includes a weight measurement means for measuring a weight of a user, a bioelectrical impedance measurement means for measuring a bioelectrical impedance of a user by BIA, a date and time identification means for identifying a date and time of measurement, and a calculating means for calculating the low-precision in-body information by inputting at least the bioelectrical impedance as the measured values into the algorithm.

Whether a measurement method is low-precision or high-precision is determined relatively. In general, the measurement unit in a BIA body composition analyzer can measure in-body information with higher precision if it has more types of frequencies of applied current, more electrodes, and if it can measure each part of the body rather than only the whole body. For example, the measurement precision of the in-body information is higher in the measurement unit of a multi-frequency and multi-electrode BIA body composition analyzer than in the measurement unit of a single-frequency four-electrode BIA body composition analyzer, and the measurement precision of the in-body information is higher in the measurement unit of a site-specific BIA body composition analyzer than in the measurement unit of a whole-body method BIA body composition analyzer. In this embodiment, the low-precision measuring unit 104 is a measuring unit of the single-frequency four-electrode system that measures the low-precision in-body information.

The output unit 106 is an output means to output the measurement results of the user. The output unit 106 is, for example, an LCD (Liquid Crystal Display), an OLED (Organic Light Emitting Diode), and the like. The output unit 106 may be integrated with the simplified BIA body composition analyzer 100, or may not be integrated with the simplified BIA body composition analyzer 100, such as a smartphone or tablet computer. In this embodiment, the output unit 106 is an LCD integrated with the simplified BIA body composition analyzer 100.

The output unit 106 outputs the measurement results of the user. The output may be, for example, a display of numerical values, text, a diagram of the body shape, or the like reflecting the measurement results of the user, or it may be an audio or other form of output. In this embodiment, the output unit 106 displays the weight and low-precision in-body information measured by the low-precision measurement unit 104, corrected in-body information to be described later, information related to the measurement precision, and an alert to urge measurement of a high-precision reference value.

Figure 2:
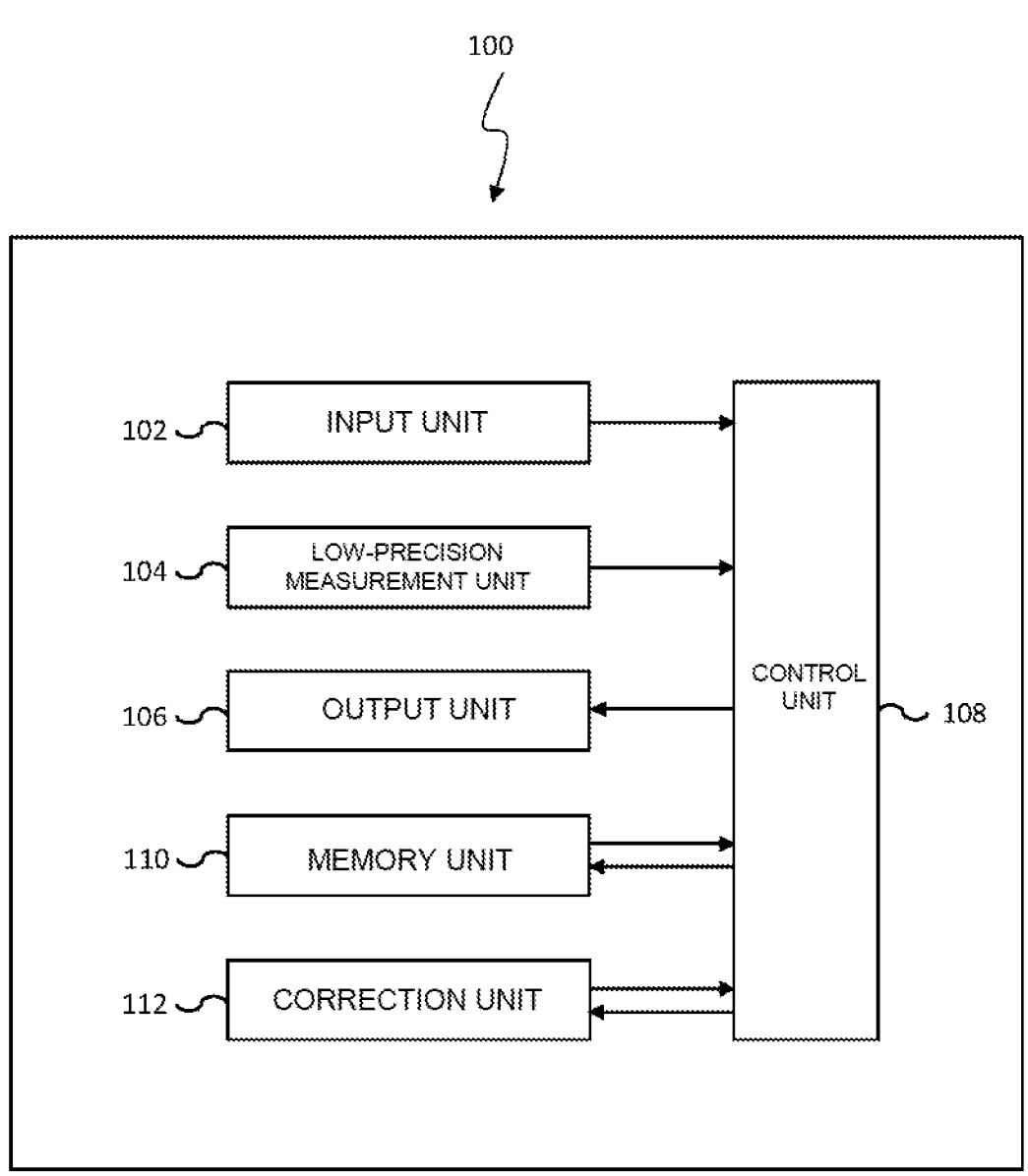
FIG. 2 shows a block diagram of the functional configuration of the simplified BIA body composition analyzer according to an embodiment.

FIG. 2 is a block diagram showing the functional configuration of a simplified BIA body composition analyzer 100 according to one embodiment of the present disclosure. The simplified BIA body composition analyzer 100 has a control unit 108, a memory unit 110, and a correction unit 112, in addition to an input unit 102, a low-precision measurement unit 104, and an output unit 106 as shown in FIG. 1.

The control unit 108 is a control device that controls the input unit 102, the low-precision measurement unit 104, the output unit 106, the memory unit 110, and the correction unit 112. The control unit 108 has a CPU (Central Processing Unit). The control unit 108 is connected to each of the units by electrical communication. The control unit 108 realizes the functions of each unit by executing a program stored in the memory unit 110. The program may be downloaded in the simplified BIA body composition analyzer 100 having a communication function, or may be read from a portable non-transitory storage medium and imported into the simplified BIA body composition analyzer 100.

The memory unit 110 is a memory that is capable of storing data. The memory may be, for example, volatile memory (e.g., RAM) or non-volatile memory (e.g., ROM). The memory unit 110 may be built into the simplified BIA body composition analyzer 100, as shown in FIG. 2, or may be provided outside the simplified BIA body composition analyzer 100, such as an external hard disk drive, an external server, or the like. In the present embodiment, the memory unit 110 is built into the simplified BIA body composition analyzer 100.

The memory unit 110 stores a program executed by the control unit 108, a correction function to be described later, and corrected in-body information.

The memory unit 110 also stores information input to the input unit 102. Specifically, the memory unit 110 stores information such as age, height, gender, high-precision reference value, weight at the time of measurement of high-precision in-body information, and date and time of measurement, which are input to the input unit 102.

The memory unit 110 stores the information used by the low-precision measurement unit 104. Specifically, the storage unit 110 stores, as information used by the low-precision measurement unit 104, information such as, for example, the weight, age, height, and gender of the user in general, statistical information related to the in-body information, and a predetermined algorithm (e.g., a regression equation, etc.) for obtaining the low-precision in-body information from the measured values obtained in the low-precision measurement.

Further, the memory unit 110 stores information acquired by the low-precision measurement unit 104. Specifically, the memory unit 110 stores information acquired by the low-precision measurement unit 104, such as, for example, body weight, bioelectrical impedance, low-precision in-body information, date and time of measurement, and corrected in-body information to be described later.

The correction unit 112 is a correction means for correcting the algorithm or the low-precision in-body information based on the high-precision reference value stored in the memory unit 110 and the degree of importance (adjustment parameter) of the reference value. The adjustment parameter is, for example, a parameter that adjusts the high-precision reference value by multiplying or subtracting it from the high-precision reference value. The correction unit 112 may be built into the simplified BIA body composition analyzer 100, as shown in FIG. 2, or may be provided outside the simplified BIA body composition analyzer 100, such as on an external server. In the present embodiment, the correction unit 112 is built into the simplified BIA body composition analyzer 100.

As described above, since the measurement in the low-precision measurement unit 104 is relatively low-precision, even if measuring the body composition same as that of the body composition at the time of the high-precision measurement (hereinafter referred to as the "a high-precision measurement time"), there may be a difference between the low-precision in-body information measured by the low-precision measurement unit 104 and the high-precision reference value. Therefore, the correction unit 112 of this embodiment determines a correction function for correcting the low-precision in-body information so as to decrease this difference. As described above, since the measurement in the low-precision measurement unit 104 is relatively low-precision, even if measuring the body composition same as that of the body composition at the time of the high-precision measurement (hereinafter referred to as the "a high-precision measurement time"), there may be a difference between the low-precision in-body information measured by the low-precision measurement unit 104 and the high-precision reference value. Therefore, the correction unit 112 of this embodiment determines a correction function for correcting the low-precision in-body information so as to decrease this difference.

However, in order to consider the difference between the high-precision reference value and the low-precision in-body information (low-precision reference value) at the time of measurement of the low-precision in-body information (low-precision measurement time) for determining the correction function to be caused by the measurement precision of the low-precision measurement unit 104, it is desirable that the body composition at the high-precision measurement time and the body composition at the low-precision measurement time are the same or extremely close. This is because, if the body compositions (i.e., true values) at the two points in time are different, the ratio of that is caused by the change in body composition and that is caused by the measurement precision of the low-precision measurement unit 104 in the difference between the high-precision reference value and the low-precision reference value will be unknown.

Therefore, the correction unit 112 calculates the contribution of the high-precision reference value to the low-precision reference value used for determining the adjustment parameter (hereinafter referred to as the "contribution of the high-precision reference value") according to the possibility or degree of difference between the body composition at the high-precision base measurement and the body composition at the low-precision measurement, and determines the adjustment parameters according to this contribution. The contribution of the high-precision reference value is determined based on the predetermined conditions exemplified below in light of the above circumstances. Since the timing to determine the correction method based on the adjustment parameters is typically immediately after the low-precision measurement, the timing to determine the correction method may be regarded as the time of the low-precision measurement for convenience (although it is strictly different from the timing of the low-precision measurement). Of course, if the timing for determining the correction method deviates relatively greatly from the timing when the low-precision measurement is made, it is desirable to use the time when the low-precision measurement is made as the low-precision measurement time.

The predetermined condition is, for example, the absolute value of the difference between the weight at the high-precision measurement time and the weight at the low-precision measurement time (hereinafter referred to as "weight difference") as an index.

Specifically, when the weight difference is smaller than $\alpha$ (weight difference$<\alpha$), the weight discrepancy is small, and thus the change in body composition is considered to be small between the high-precision measurement time and the low-precision measurement time, and the contribution of the high-precision reference value is determined to be large. In this case, the correction unit 112 determines the adjustment parameter $Y_0$ according to the contribution of the high-precision reference value, and adjusts the high-precision reference value by the primary adjustment "$Y_0 \times$high-precision reference value" in which $Y_0$ is multiplied by the high-precision reference value. For the specific value of $Y_0$, different values are used for cases where the body weight increased and decreased, and different values are used for different types of in-body information (e.g., body fat, muscle mass, body water content, etc.) that is used as the high-precision reference value.

When the body weight at the low-precision measurement time increases compared to the body weight at the high-precision measurement time, $Y_0$ used to adjust the body fat (amount/percentage) as the high-precision reference value, shall be a value slightly less than 1 or 1, $Y_0$ used to adjust the muscle mass shall be a value slightly greater than 1 or 1, and $Y_0$ used to adjust the body water content shall be a value slightly greater than 1 or 1. Setting $Y_0$ to 1 is synonymous with not performing the primary adjustment.

When the body weight at the low-precision measurement time decreases compared to the body weight at the high-precision measurement time, $Y_0$ used to adjust the body fat (amount or percentage) as the high-precision reference value, shall be a value slightly greater than 1 or 1, $Y_0$ used to adjust the muscle mass shall be a value slightly less than 1 or 1, and $Y_0$ used to adjust the body water content shall be a value slightly less than 1 or 1.

When the weight difference is greater than or equal to $\alpha$ but less than $\beta$ (weight difference$<\beta$), it is considered that there is a change in body composition between the high-precision measurement time and the low-precision measurement time because there is some extent of weight discrepancy more than that in the case of "weight difference$<\alpha$." The contribution of the high-precision reference value to the low-precision reference value is determined to decrease as the weight difference increases. In this case, the correction unit 112 determines the adjustment parameters $Y_1$ to $Y_5$ (hereinafter referred to as "$Y_{1-5}$") according to the contribution of the high-precision reference value, and adjust the high-precision reference value by a primary adjustment "$Y_{1-5} \times$high-precision reference value" in which $Y_{1-5}$ is multiplied by the high-precision reference value. As the specific values of $Y_{1-5}$, as with $Y_0$, different values are used for cases where the body weight increased and decreased, and different values are used for different types of in-body information as the high-precision reference values (e.g., body fat mass, muscle mass, body weight, and body weight).

When the body weight at the low-precision measurement time increases compared to the body weight at the high-precision measurement time, $Y_{1-5}$ used for the adjustment of body fat (amount/percentage) as the high-precision reference value, shall be smaller than 1, $Y_{1-5}$ used for the adjustment of muscle mass shall be larger than 1, and $Y_{1-5}$ used for the adjustment of body water content shall be larger than 1.

On the other hand, when the body weight at the low-precision measurement time decreases compared to the body weight at the high-precision measurement time, $Y_{1-5}$ used for the adjustment of body fat (amount/percentage) as the high-precision reference value, shall be a value greater than 1, $Y_{1-5}$ used for the adjustment of muscle mass shall be a value less than 1, and $Y_{1-5}$ used for the adjustment of body water content shall be a value less than 1.

When the weight difference is $\beta$ or more (weight difference$\geq\beta$), and the absolute value of the difference between the high-precision reference value and the low-precision in-body information from the simplified BIA body composition analyzer 100 (hereinafter referred to as the "in-body difference") is $\gamma$ or more (body weight difference$\geq\gamma$), since a weight deviation is observed, the contribution of the high-precision reference value is determined to be somewhat low in order to reflect the user's body composition that deviates significantly from the average body composition estimated from statistical values, although there is a change in body composition between the high-precision measurement time and the low-precision measurement time. In this case, the high-precision reference value is adjusted by the same primary adjustment "$Y_{1-5}\times$high-precision reference value" as in "weight difference$<\beta$".

When the above-mentioned conditions pertaining to the weight difference and the in-body difference are not satisfied, it is considered that there is a large change in body composition between the high-precision measurement time and the low-precision measurement time, and the contribution of the high-precision reference value is determined to be small. In this case, the correction unit 112 does not perform any correction based on the high-precision reference value adjusted by the adjustment parameter.

As a predetermined condition, for example, the period of time from the high-precision measurement time to the low-precision measurement time (hereinafter referred to as "elapsed days") can be used as an index.

Specifically, when the number of the elapsed days is "z1 days or less," since the number of the elapsed days is relatively short, the change in body composition between the high-precision measurement time and the low-precision measurement time is considered to be small, and the contribution of the high-precision reference value is determined to be large. In this case, the correction unit 112 performs only the primary adjustment and does not perform the adjustment of the high-precision reference value based on the elapsed days (secondary adjustment).

When the number of elapsed days is "within z2 days" although z1 days have elapsed, since there is a certain number of elapsed days, it is considered that there is a change in body composition between the high-precision measurement time and the low-precision measurement time, and the contribution of the high-precision reference value is determined to be slightly low. At this time, the correction unit 112 adjusts the primarily adjusted high-precision reference value using the low-precision reference value according to the contribution of the high-precision reference value. Specifically, the correction unit 112 adjusts the high-precision reference value by the secondary adjustment "$(a\times Y_{0-5}\times$high-precision reference value$+b\times$low-precision reference value)/2". The secondary adjustment parameters a and b may, for example, satisfy $0<a<1$ and $b=1-a$. The longer the elapsed days are, the smaller the value of a and the larger the value of b.

As the primary adjustment parameters $Y_{0-5}$ when secondary adjustment is performed (i.e., when the elapsed days are greater than z1 and within z2), different values may be adopted from those of $Y_{0-5}$ when only primary adjustment is performed (i.e., when the elapsed days are within z1). This is because when the number of elapsed days is "within z1 days," i.e., when the number of elapsed days is relatively short, the reason for the weight difference can be considered to be a change in body water content, whereas when the number of elapsed days exceeds z1 days, i.e., when the number of elapsed days is relatively long, it is difficult to identify the reason for the weight difference, and thus the reason for the weight difference is different when the elapsed days are short and when the elapsed days are long.

When the weight at the low-precision measurement time increases compared to the weight at the high-precision measurement time, $Y_{0-5}$, which are used to adjust the high-precision reference values of body fat (volume or percentage), muscle mass, and body water content, shall all be set to a value of 1 or higher.

On the other hand, when the body weight at the low-precision measurement time decreases compared to the body weight at the high-precision measurement time, $Y_{0-5}$, which are used to adjust the high-precision reference values of body fat (volume or percentage), muscle mass, and body water content, shall all be set to a value less than or equal to 1.

If the condition pertaining to the number of elapsed days described above is not satisfied, that is, if the number of elapsed days is z2 or more, the change in body composition between the high-precision measurement time and the low-precision measurement time is considered to be large, and the contribution of the high-precision reference value is determined to be low. In this case, the correction unit 112 does not determine the adjustment parameter and does not adjust the high-precision reference value.

However, when the primary adjustment "$Y_{0-5}\times$high-precision reference value" is performed and the elapsed days are greater than z2 days, but the user selects the secondary adjustment (hereinafter referred to as "adjustment selection"), the adjustment parameters for the secondary adjustment may be determined, and the high-precision reference value may be adjusted by the secondary adjustment "$(a\times Y_{0-5}\times$high-precision reference value$+b\times$low-precision reference value)/2".

Compared to the number of elapsed days, the weight difference has a greater influence on the change in body composition. Therefore, the adjustment parameters $Y_{0-5}$ of the primary adjustment, which reflect the contribution of the high-precision reference value, are parameters that are greatly affected by the weight difference. On the other hand, the adjustment parameters a and b of the secondary adjustment, which also reflect the contribution of the high-precision reference value, are parameters that are not so greatly affected by the number of days elapsed. In other words, there is a qualitative difference between the adjustment parameters $Y_{0-5}$ of the primary adjustment and the adjustment parameters a and b of the secondary adjustment in terms of the degree of influence of the weight difference and the number of days elapsed on the parameters.

Since the predetermined condition is a condition for determining the contribution of the high-precision reference value, for example, the ratio of the weight at the high-precision measurement time to the weight at the low-precision measurement time may be used as an indicator.

When the predetermined condition is based on the weight difference as an indicator, instead of being divided into three levels: "weight difference$<\alpha$", "weight difference$<\beta$", and "weight difference$\geq\beta$", it may be divided into fewer or more levels. Similarly, when the predetermined condition is based on the number of days elapsed as an indicator, instead of being divided into two levels: "within z1 days", and "within z2 days", it may be divided into fewer or more levels.

In addition, the adjustment of the high-precision reference value is not limited to the primary adjustment followed by the secondary adjustment, but may also include a tertiary or higher adjustment, for example, by further weighting after the secondary adjustment. That is, the formula for calculating the adjusted high-precision reference value may be obtained by using the formula for several adjustments.

As described above, when the adjustment parameter is determined and the high-precision reference value is adjusted, the correction unit 112 determines a correction function that relates the corrected in-body information to the low-precision in-body information based on the high-precision reference value adjusted using the adjustment parameter and the low-precision reference value. The correction function is then used to correct the low-precision in-body information to obtain the corrected in-body information. In the measurement after the determination of the correction function, the correction unit 112 obtains the corrected in-body information by correcting the low-precision in-body information calculated by the low-precision measurement unit 104 using the predetermined algorithm with this correction function. When a high-precision reference value is newly obtained, the correction function can be updated.

The correction function may be one of the following (1), (2), or (3), for example:

(Corrected in-body information)=$c$×(Low-precision in-body information)+$d$    (1)

(Corrected in-body information)=$c$×(Low-precision in-body information)    (2)

(Corrected in-body information)=(Low-precision in-body information)+$d$    (3)

The parameters c and d of the correction function are determined to satisfy the following (1'), (2'), and (3') for the equations (1), (2), and (3), respectively:

(Adjusted high-precision reference value)=$c$×(Low-precision reference value)+$d$    (1')

(Adjusted high-precision reference value)=$c$×(Low-precision reference value)    (2")

(Adjusted high-precision reference value)=(Low-precision reference value)+$d$    (3")

(Operation of the Body Composition Analyzer of the First Embodiment)

The following describes a flow that realizes the operation of the body composition analyzer according to the first embodiment with the above-mentioned configuration of the body composition analyzer. This flow can be performed each time a high-precision reference value is input to the simplified BIA body composition analyzer 100. In this flow, the high-precision reference value and the low-precision reference value are used to determine a correction function. In the measurement after the correction function is determined, this correction function can be used to correct the low-precision in-body information.

Figure 3:
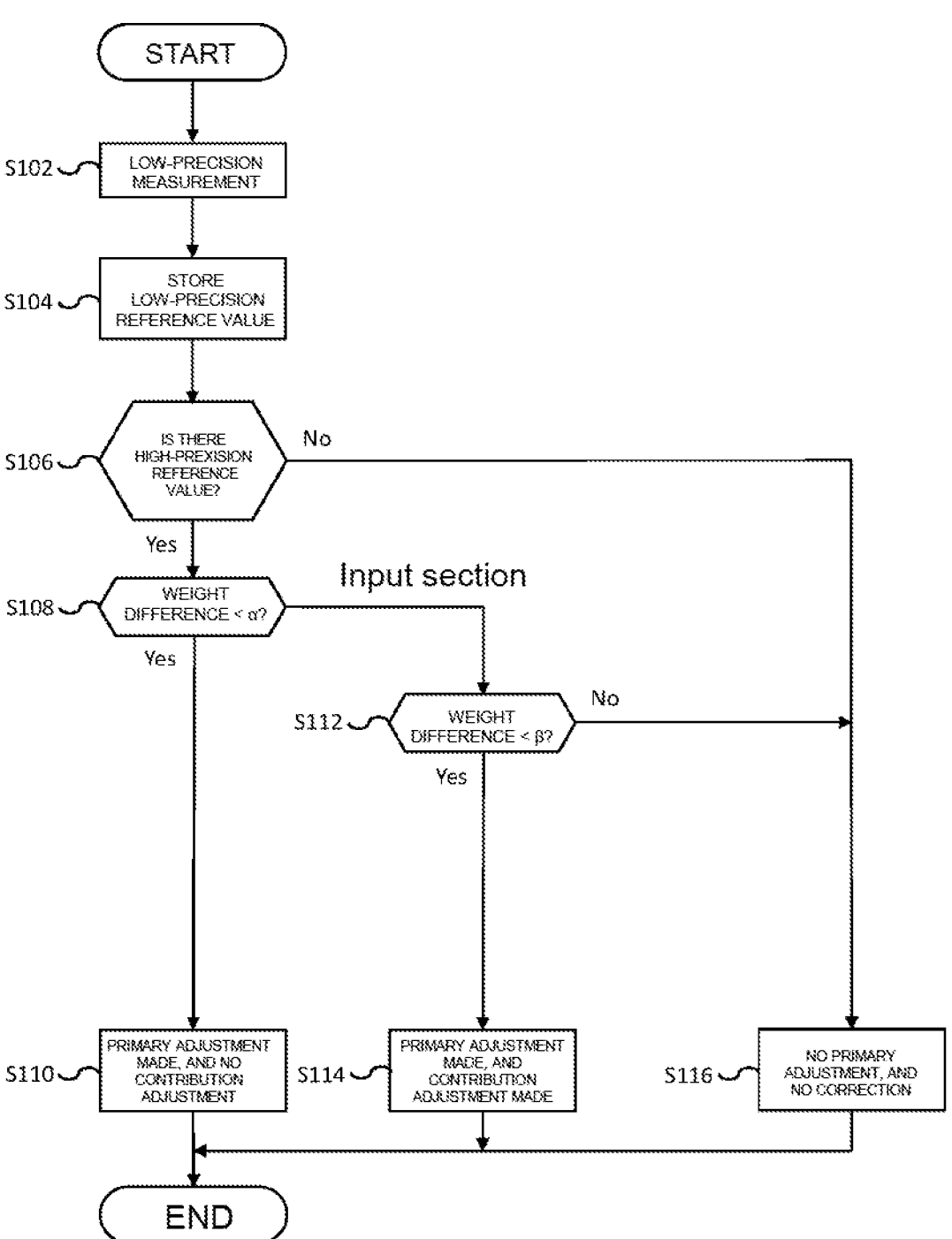
FIG. 3 is a first flowchart showing operations of a simplified BIA body composition analyzer for determining the correction function according to the first embodiment.

FIG. 3 is a first flowchart showing the operation of a simplified BIA body composition analyzer 100 for determining a correction function according to the first embodiment of the present disclosure. The first flow in the first embodiment is a flow for primary adjustment of high-precision in-body information using weight difference as an indicator. The first flow starts when a user operates the simplified BIA body composition analyzer 100 to start the process of determining the correction function.

First, the user's in-body information is measured by the low-precision measurement unit 104 (Step S102).

When the low-precision measurement unit 104 measures the in-body information of the user, the memory unit 110 stores the low-precision reference value (Step S104).

When the memory unit 110 stores the low-precision reference value, the correction unit 112 determines the presence or absence of the high-precision reference value (Step S106) stored in the memory unit 110 and the weight difference (Step S108).

When it is determined that "there is a high-precision reference value" stored in the memory unit 110 and "weight difference<$\alpha$" (Step S106: Yes, Step S108: Yes), the correction unit 112 determines the adjustment parameter $Y_0$ according to the contribution of the high-precision reference value, adjusts the high-precision reference value by the primary adjustment "$Y_0$×high-precision reference value" (Step S110), and the flow ends.

That is, when it is determined that "weight difference<$\alpha$", the weight deviation is small, so the change in body composition is considered to be small between the high-precision measurement time and the low-precision measurement time, and the contribution of the high-precision reference value is determined to be large. In this case, the correction unit 112 determines the adjustment parameter $Y_0$ according to the contribution of the high-precision reference value, and adjusts the high-precision reference value by the primary adjustment "$Y_0$×high-precision reference value".

On the other hand, if it is determined that "there is a high-precision reference value" stored in the memory unit 110 and the weight difference is not "weight difference<$\alpha$" (Step S106: Yes, Step S108: No), the correction unit 112 determines the weight difference again (Step S112). When it is determined that "weight difference<$\beta$" (Step S112: Yes), the correction unit 112 determines the adjustment parameters $Y_{1-5}$ according to the contribution of the high-precision reference value, and adjusts the high-precision reference value by the primary adjustment "$Y_{1-5}$×high-precision reference value" (Step S114), and the flow ends.

That is, when it is determined that "weight difference<$\beta$", the contribution of the high-precision reference value is determined to be somewhat low, because the weight deviation is seen to some extent more than when it is determined that "weight difference<$\alpha$", so it is considered that there is a change in body composition between the high-precision measurement time and the low-precision measurement time. In this case, the correction unit 112 determines the adjustment parameters $Y_{1-5}$ according to the contribution of the high-precision reference value, and adjusts the high-precision reference value by the primary adjustment "$Y_{1-5}$×high-precision reference value".

On the other hand, if it is determined that it is not "there is a high-precision reference value" stored in the memory unit 110 (Step S106: No) or that it is "there is a high-precision reference value" but not "weight difference<$\alpha$" and not "weight difference<$\beta$" (Step S106: Yes, Step S108: No, Step S112 (Step S106: Yes, Step S108: No, Step S112: No), the correction unit 112 does not correct the low-precision reference value by the correction function based on the primarily adjusted high-precision reference value (Step S116), it merely is that the storage unit 110 stores the high-precision reference value as a reference value, and the flow ends.

That is, when it is determined that "there is a high-precision reference value" but not "weight difference<$\alpha$"

nor "weight difference<$\beta$", it is considered that the change in body composition between the high-precision measurement time and the low-precision measurement time is large, and the contribution of the high-precision reference value is small. In this case, the correction unit 112 does not make any correction.

As described above, in the first flow in the first embodiment, the contribution of the high-precision reference value is evaluated using the weight deviation as an indicator. When the weight deviation is small (weight difference<$\alpha$), the high-precision reference value is adjusted by the primary adjustment "$Y_0 \times$high-precision reference value"; when some weight deviation is observed (weight difference<$\beta$), the high-precision reference value is adjusted by the primary adjustment "$Y_{1-5} \times$high-precision reference value"; and when the weight deviation is large (weight difference$\geq \beta$), no correction is made.

Thus, in the first flow in the first embodiment, even if there is some change in body composition between the high-precision measurement time and the low-precision measurement time, an adjustment parameter reflecting the contribution of the high-precision reference value is determined, and the high-precision reference value is adjusted by this adjustment parameter. In particular, in this embodiment, the contribution can be evaluated based on the difference in body weight independent of the difference in measurement methods, and the adjustment parameters reflecting the contribution in detail can be determined.

In other words, even if the low-precision in-body information is to be corrected when a difference arises between the high-precision reference value and the low-precision reference value, it is necessary to determine whether such difference is caused by the measurement precision of the simplified BIA body composition analyzer 100 or by a change in the body composition of the user.

Therefore, when the weight difference is used as an indicator and the weight difference is small and the identity of the body composition of the user can be ensured, the difference between the high-precision reference value and the low-precision reference value is determined to be caused by the measurement precision of the simplified BIA body composition analyzer 100, and the adjustment parameter is determined so that the contribution of the high-precision reference value becomes large.

On the other hand, when the weight difference is large and the identity of the body composition of the user cannot be ensured, the difference between the high-precision reference value and the low-precision reference value is determined to be caused by the change in the body composition of the user, and the adjustment parameters are determined so that the contribution of the high-precision reference value becomes small. Therefore, it is possible to provide a highly precise body measurement system and program tailored to individuals.

Figure 4:
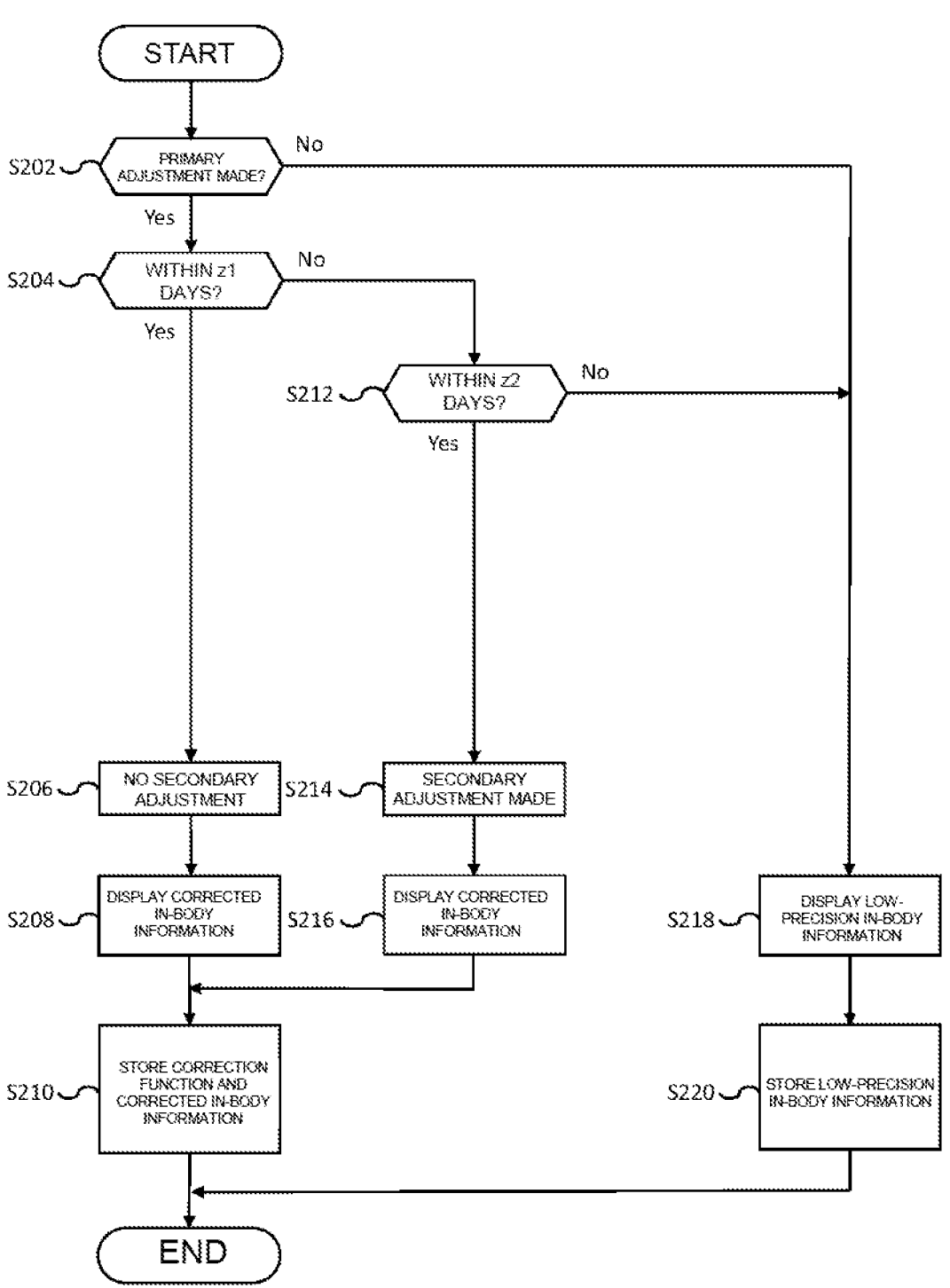
FIG. 4 shows a second flowchart showing operations of the simplified BIA body composition analyzer for determining the correction function according to the first embodiment.

FIG. 4 is a second flowchart showing the operation of the simplified BIA body composition analyzer 100 for determining the correction function according to the first embodiment of the present disclosure. The second flow is a flow for further secondary adjustment of the primarily adjusted high-precision reference value using the number of days elapsed from the high-precision measurement time to the low-precision measurement time as an indicator. After the first flow is completed, the second flow starts.

When the second flow starts, the correction unit 112 determines whether the primary adjustment has been made (Step S202) and the number of elapsed days (Step S204).

When it is determined that "primary adjustment made" and the number of elapsed days is "within z1 days" (Step S202: Yes, Step S204: Yes), the correction unit 112 determines a correction function based on the primarily adjusted high-precision reference value without performing secondary adjustment (Step S206), and corrects the low-precision reference value by this correction function. The output unit 106 displays the low-precision in-body information as the corrected low-precision reference value as the corrected in-body information (Step S208). Then, the memory unit 110 stores the correction function and the corrected in-body information (Step S210), and the flow ends.

That is, when the primary adjustment is made and the number of elapsed days is "within z1 days," the change in body composition is considered to be small between the high-precision measurement time and the low-precision measurement time, and the contribution of the high-precision reference value is determined to be high. In this case, the correction unit 112 does not perform the secondary adjustment.

On the other hand, when it is determined that "primary adjustment made" and the number of elapsed days is not "within z1 days" (Step S202: Yes, Step S204: No), the correction unit 112 determines the number of elapsed days again (Step S212).

When the number of elapsed days is determined to be "within z2 days" (Step S212: Yes), the correction unit 112 determines the adjustment parameters $Y_{0-5}$, a, and b according to the contribution of the high-precision reference value, and adjusts the high-precision reference value by the secondary adjustment "(a$\times Y_{0-5} \times$high-precision reference value+b$\times$low-precision reference value)/2" (Step S214). Then, the correction unit 112 determines a correction function based on the secondarily adjusted high-precision reference value and corrects the low-precision reference value by this correction function, the output unit 106 displays the low-precision in-body information as the corrected low-precision reference value as the corrected in-body information (Step S216), the memory unit 110 stores the correction function and the corrected in-body information (Step S210), and the flow ends.

That is, when it is determined that "primary adjustment made" and the number of elapsed days is "within z2 days," it is considered that there is a change in body composition between the high-precision measurement time and the low-precision measurement time, and the contribution of the high-precision reference value is determined to be slightly low. At this time, the correction unit 112 determines the adjustment parameters $Y_{0-5}$, a, and b according to the contribution of the high-precision reference value, and adjusts the high-precision reference value by the secondary adjustment "(a$\times Y_{0-5} \times$high-precision reference value+b$\times$low-precision reference value)/2".

On the other hand, if it is determined that it is not "primary adjustment made" (Step S202: No) or that it is "primary adjustment made" and the elapsed days are not "within z2 days" (Step S202: Yes, Step S204: No, Step S212: No), the correction unit 112 adjusts the low-precision reference value by the correction function. The output unit 106 displays the low-precision in-body information as the low-precision reference value (Step S218), the memory unit 110 stores the low-precision in-body information as the low-precision reference value (Step S220), and the flow ends.

That is, when it is not determined "primary adjustment made", or when it is not determined that the number of elapsed days is "within z2 days" even if "primary adjustment made" is determined, the change in body composition between the high-precision measurement time and the low-precision measurement time is considered to be large, and the contribution of the high-precision reference value is determined to be small. In this case, the correction unit 112 does not make any correction.

As described above, in the second flow in the first embodiment, the contribution of the high-precision reference value is evaluated using the number of elapsed days as an indicator. When the primary adjustment is performed and the number of days has hardly elapsed (within z1 days), the low-precision in-body information as the low-precision reference value is corrected by a correction function based on the primarily adjusted high-precision reference value, the low-precision in-body information as the corrected low-precision reference value is displayed as the corrected in-body information, and the correction function and the corrected in-body information are stores.

When the number of days has lapsed to some extent (within z2 days), the low-precision in-body information as the low-precision reference value is corrected using a correction function based on the secondarily adjusted high-precision reference value, and the corrected low-precision in-body information as the low-precision reference value is displayed as the corrected in-body information, and the correction function and the corrected in-body information are stored.

When the primary adjustment is not performed, or when the number of days has passed z2 even if the primary adjustment is performed, the low-precision in-body information as the low-precision reference value is displayed without correction by the correction function, and the low-precision in-body information as the low-precision reference value is stored.

Thus, in the second flow, even if there is some change in body composition between the high-precision measurement time and the low-precision measurement time, the adjustment parameter reflecting the contribution of the high-precision reference value is determined, and the high-precision reference value is adjusted by this adjustment parameter, so that the correction function can be determined using the high-precision reference value and the low-precision reference value. In particular, in this embodiment, the contribution of the high-precision reference value can be evaluated based on the lapsed time, and determine adjustment parameters that reflect the contribution of the high-precision reference value in detail.

In other words, when a difference arises between the high-precision reference value and the low-precision in-body information as the low-precision reference value at the low-precision measurement time, even if the low-precision in-body information as the low-precision reference value is to be corrected, it is necessary to determine whether such difference is caused by the measurement precision of the simplified BIA body composition analyzer 100 or by changes in the body composition of the user.

Therefore, using the lapsed time as an indicator, when time has not lapsed so much and the identity of the body composition of the user can be ensured, the difference between the high-precision reference value and the low-precision in-body information as the low-precision reference value at the low-precision measurement time is determined to be caused by the measurement precision of the simplified BIA body composition 100, and the adjustment parameter is determined so that the contribution of the high-precision reference value becomes large.

On the other hand, when time has lapsed and the identity of the body composition of the user cannot be ensured, the difference between the high-precision reference value and the low-precision in-body information as the low-precision reference value at the time of the low-precision measurement time is determined to be caused by the change in the body composition of the user, and the adjustment parameter is determined so that the contribution of the high-precision reference value becomes small. Therefore, it is possible to provide a highly precise body measurement system and program tailored to individuals.

In addition, in the second flow, since the correction function and the corrected in-body information can be stored, by reflecting the correction function and the corrected in-body information in future in-body measurements, the more the simplified BIA body composition analyzer 100 is used, the more the individual differences can be reflected with high-precision, and thus a highly precise in-body measurement system and program tailored to individuals can be provided.

In addition, since the evaluation is not performed only by a predetermined algorithm (e.g., regression equation) but also by an individual-correction function tailored to an individual's high-precision reference value, it is possible to adapt the results of body composition measurement to high-precision body composition corresponding to individual differences even though it is a simple measurement. In addition, the relative changes from the values can be tracked by the simplified BIA body composition analyzer 100, so that, unlike the body composition measurement (estimation) method and the high-precision BIA body composition analyzer, which cannot be measured easily, the detailed daily changes can be captured in a timely manner when they are needed without missing them, and the advantages of both can be combined, thus it is possible to provide a highly precise body measurement system and program tailored to individuals.

In addition, by subordinating the second flow, which reflects low-precision in-body information as low-precision reference values via adjustment parameters a and b, to the first flow, which reflects only high-precision reference values via adjustment parameters $Y_{0-5}$, excessive correction by the first flow can be prevented, thus providing a highly precise intra-body measurement system and program tailored to individuals.

Figure 5A:
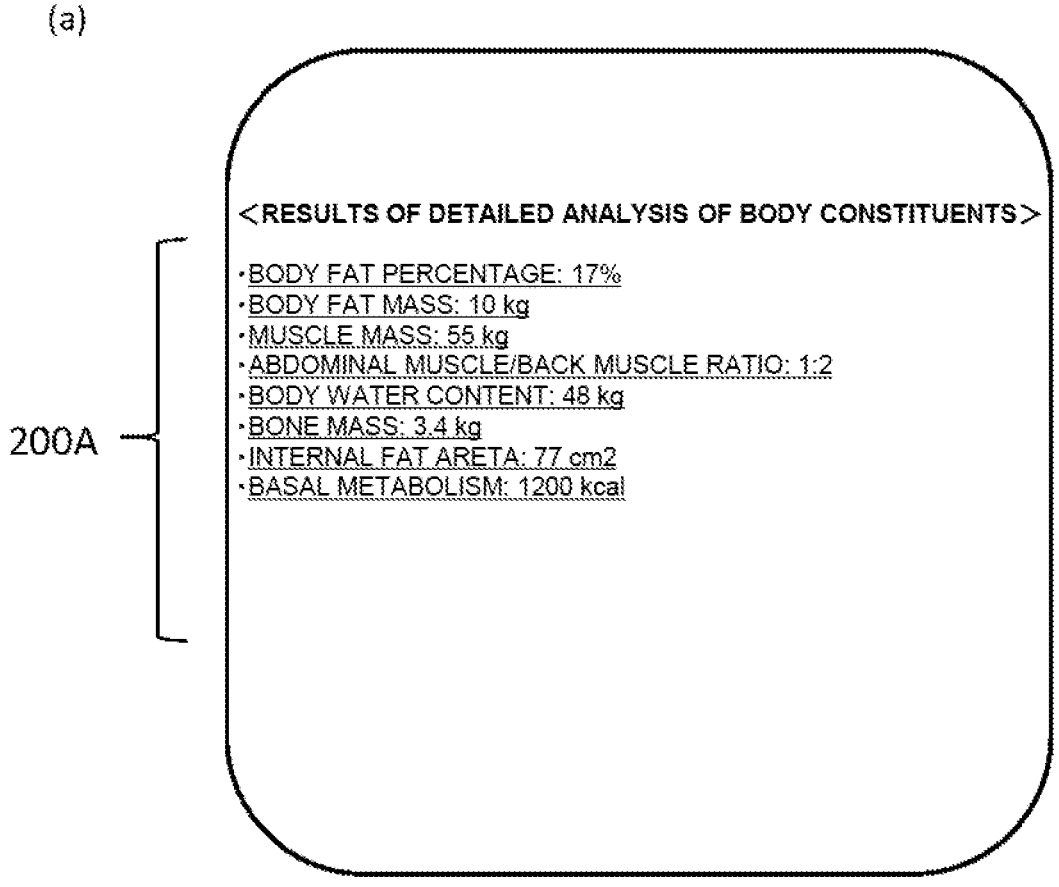
FIG. 5A shows a first result display screen of the simplified BIA body composition analyzer according to the first embodiment.

FIG. 5A shows the first result display screen of the simplified BIA body composition analyzer 100 according to the first embodiment of the present disclosure, and FIG. 5B shows the second result display screen of the simplified BIA body composition analyzer 100 according to the first embodiment of the present disclosure.

As shown in FIG. 5A, the output unit 106 displays the corrected in-body information 200A. For example, the output unit 106 displays as the corrected in-body information 200A: body fat percentage: 17%, body fat mass: 10 kg, muscle mass: 55 kg, abdominal muscle/back muscle ratio: 1:2, body water content: 48 kg, bone mass: 3.4 kg, internal fat area: 77 $cm^2$, and basal metabolism: 1200 kcal. This allows the user to know the corrected in-body information.

As shown in FIG. 5B, the output unit 106 displays the corrected in-body information 200B in a different appearance so that it can be distinguished from the low-precision in-body information. Displaying the information in a different appearance means displaying it with a mark such as a star, displaying it in a different font, size, and/or color, and displaying the fact that the body composition measurement (estimation) method and the high-precision BIA body composition analyzer are referred to.

In this embodiment, the output unit 106 displays "(star mark) Body fat percentage: 17% (DXA referenced!), (star mark) Muscle mass: 55 kg (DXA-referenced!), (star mark) Abdominal to back muscle ratio: 1:2 (MRI-referenced!), (star mark) Body water content: 48 kg (refer to heavy water dilution method!), (star mark) Bone mass: 3.4 kg (DXA-referenced!), (star mark) Internal fat area: 77 cm$^2$ (CT-referenced!) Basal metabolism: 1200 kcal (BIA regression equation)".

In other words, the corrected in-body information 200B excluding "Basic metabolism: 1200 kcal (BIA regression equation)" is marked with a star and displayed in association with the body composition measurement (estimation) method and the measurement method of the high-precision BIA body composition analyzer, and those are not displayed for the "Basic metabolism: 1200 kcal (BIA regression equation)", so that the appearance of the corrected in-body information 200B and the low-precision in-body information can be distinguished.

As shown in FIG. 5B, the output unit 106 displays the information 202B related to the precision of the corrected in-body information based on the degree. For example, the output unit 106 displays the information 202B related to the precision of the information in the correction body based on the degree of contribution of the high-precision reference value.

The information 202B related to the precision of the corrected in-body information is, for example, displayed as "A" when there is a high-precision reference value, and displayed as "B" when there is no high-precision reference value and only the in-body information measured with low-precision by the simplified BIA body composition analyzer 100. Furthermore, even in the case where "A" is displayed, the precision of the high-precision reference value, weight difference, and the number of elapsed days are used as indicators, and the values are ranked as A1, A2, A3, etc., in order according to the contribution of the high-precision reference value.

In this embodiment, when there is a high-precision reference value, the precision of the high-precision reference value is high, the weight difference is determined to be "weight difference<α" and the number of elapsed days is determined to be "within z1 days", the information 202B related to the precision of the information in the correction body is ranked as A1 and displayed.

In this way, the output unit 106 displays the corrected in-body information 200B in a different appearance so that it can be distinguished from the low-precision in-body information, so that the user can know whether the in-body information has been made highly precise or not. Also, by having the output unit 106 display information related to the measurement precision based on the contribution of the high-precision reference value, the user can know to what extent the measurement results have been made highly precise.

In other words, the output unit 106 can display how much the measurement result has been made more precise by inputting a high-precision reference value, and the contribution of the high-precision reference value by the reference measurement method and the number of elapsed days can also be expressed in a simplified manner, so that the user can feel the increase in precision. Therefore, it is possible to provide a highly precise body measurement system and program tailored to the individual.

(Operation of the Body Composition Analyzer in the Second Embodiment)

Since the configuration of the body composition analyzer in the second embodiment is the same as that of the body composition analyzer described above, the description thereof is omitted. Since the operation of the body composition analyzer in the second embodiment differs from that of the first embodiment described above only in the first flow, only this difference will be described below.

Figure 6:
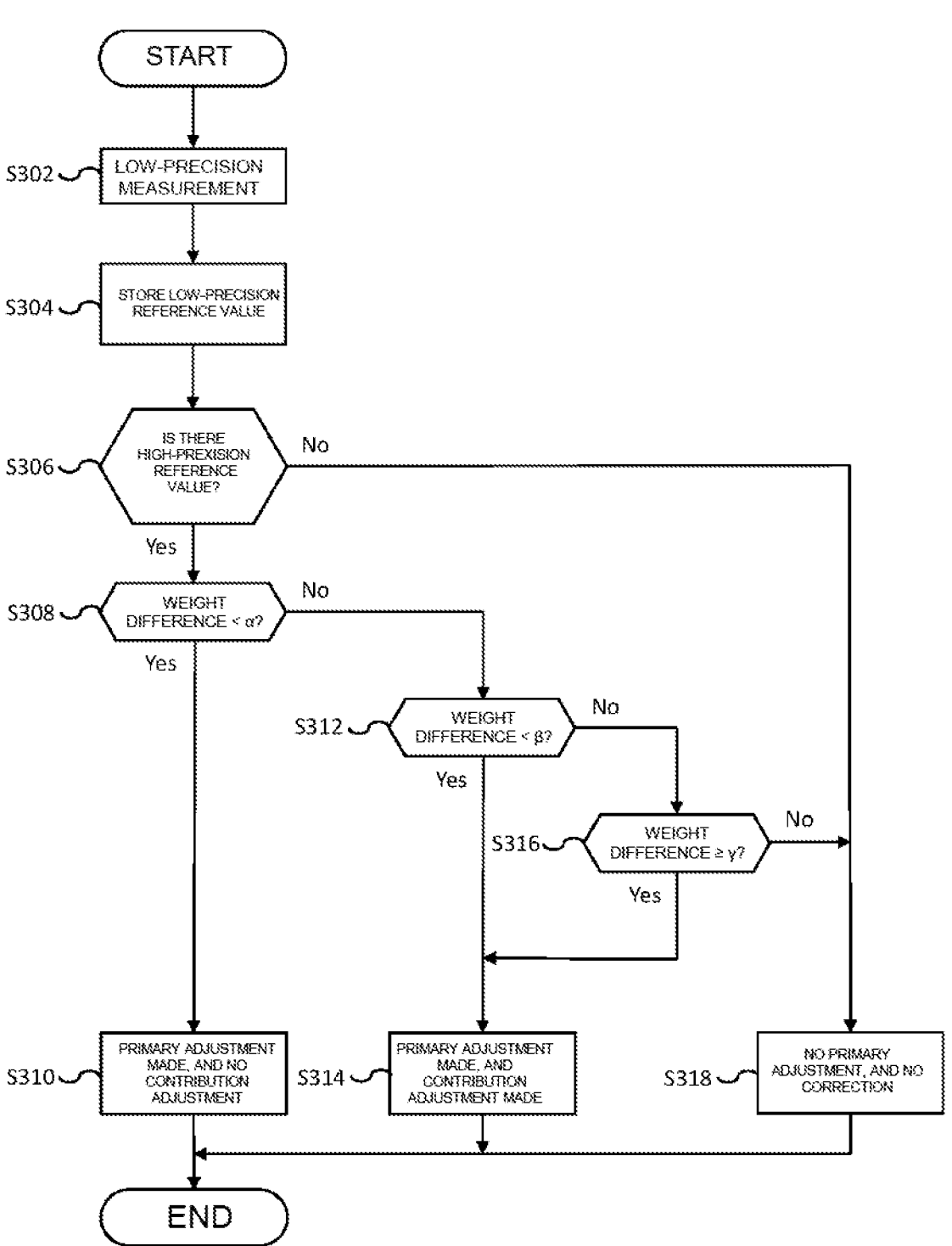
FIG. 6 shows a first flowchart showing operations of the simplified BIA body composition analyzer for determining the correction function according to the second embodiment.

FIG. 6 is a first flowchart showing the operation of the simplified BIA body composition analyzer 100 for determining the correction function in the second embodiment. The first flow in the second embodiment differs from the first flow in the first embodiment in that it is a flow for primary adjustment of the high-precision in-body information using the in-body difference as an indicator in addition to the weight difference. The first flow in the second embodiment starts when the user operates the simplified BIA body composition analyzer 100 to start the process of determining the correction function.

First, the in-body information of the user is measured by the low-precision measurement unit 104 (Step S302).

When the low-precision measurement unit 104 measures the user's in-body information, the memory unit 110 stores the low-precision reference value (Step S304).

When the memory unit 110 stores the low-precision reference value, the correction unit 112 determines the presence or absence of the high-precision reference value (Step S306) and the weight difference (Step S308) stored in the memory unit 110.

When it is determined that "there is a high-precision reference value" stored in the memory unit 110 and "weight difference<α" (Step S306: Yes, Step S308: Yes), the correction unit 112 determines the adjustment parameter $Y_0$ according to the contribution of the high-precision reference value, and adjusts the high-precision reference value by the primary adjustment "$Y_0$×high-precision reference value" (Step S310), and the flow ends.

That is, when it is determined that "weight difference<α", the weight deviation is small, so the change in body composition between the high-precision measurement time and the low-precision measurement time is considered to be small, and the contribution of the high-precision reference value is determined to be large. At this time, the correction unit 112 determines the adjustment parameter $Y_0$ according to the contribution of the high-precision reference value, and adjusts the high-precision reference value by the primary adjustment "$Y_0$×high-precision reference value.

On the other hand, when it is determined that "there is a high-precision reference value" stored in the memory unit 110 and the weight difference is not "weight difference<α" (Step S306: Yes, Step S308: No), the correction unit 112 determines the weight difference again (Step S312). Then, when it is determined that "weight difference<β" (Step S312: Yes), or when it is determined that "body weight difference≥γ" even if it is not "weight difference<β" (Step S312: No, Step S316: Yes), the correction unit 112 determines the adjustment parameters $Y_{1-5}$ according to the high-precision reference value, and adjust the high-precision reference value by the primary adjustment "$Y_{1-5}$×high-precision reference value" (Step S314), and the flow ends.

That is, when it is determined that "body weight difference≥γ" even though the body weight difference is not "body weight difference<β", because weight deviation is observed, the contribution of the high-precision reference value is somewhat low to reflect the body composition of the user that is greatly deviated from the body composition estimated from the statistical values, although there is a change in body composition between the high-precision measurement time and the low-precision measurement time. In this case, the high-precision reference value shall be adjusted by the same primary adjustment "$Y_{1-5}$×high-precision reference value" as in the case of "weight difference<$\beta$".

On the other hand, if it is determined that it is not "there is a high-precision reference value" stored in the memory unit 110 (Step S306: No), or that it is "there is a high-precision reference value" but not "weight difference<$\alpha$", not "weight difference<$\beta$", and not "in-body difference≥$\gamma$" (Step S306: Yes, Step S308: No, Step S312: No, Step S316: No), the correction unit 112 does not correct the low-precision reference value by the correction function based on the primarily adjusted high-precision reference value (Step S318), it merely is that the storage unit 110 stores the high-precision reference value as a reference value, and the flow ends.

That is, when it is determined that "there is a high-precision reference value" but not "weight difference<$\alpha$," not "weight difference<$\beta$," and not "body difference≥$\gamma$," there is no need to reflect the body composition of the user whose body composition has changed significantly between the high-precision measurement time and the low-precision measurement time, and which has deviated significantly from the body composition estimated from the statistical values. In this case, the correction unit 112 does not make any correction.

As described above, in the first flow in the second embodiment, the contribution of the high-precision reference value is evaluated using the weight difference and the body difference as indicators. Unlike the first flow for the first embodiment, even when the weight deviation is large (weight difference≥$\beta$), if the body difference is large (body difference≥$\gamma$), the high-precision reference value is adjusted by the primary adjustment "$Y_{1-5}$×high-precision reference value," and if the body difference is small, no correction is made.

Thus, unlike the first flow in the first embodiment, the first flow in the second embodiment can determine adjustment parameters that reflect the contribution of high-precision reference values based on differences in the in-body information of individuals (in-body differences) in addition to weight differences that do not depend on the measurement method. Therefore, it is possible to provide a highly precise body measurement system and program tailored to individuals.

(Operation of the Body Composition Monitor According to the Third Embodiment)

Since the configuration of the body composition analyzer in the third embodiment is the same as that of the body composition analyzer described above, the description thereof is omitted. Since the operation of the body composition analyzer in the third embodiment differs from the first embodiment described above only in the second flow, only this difference will be explained below.

Figure 7:
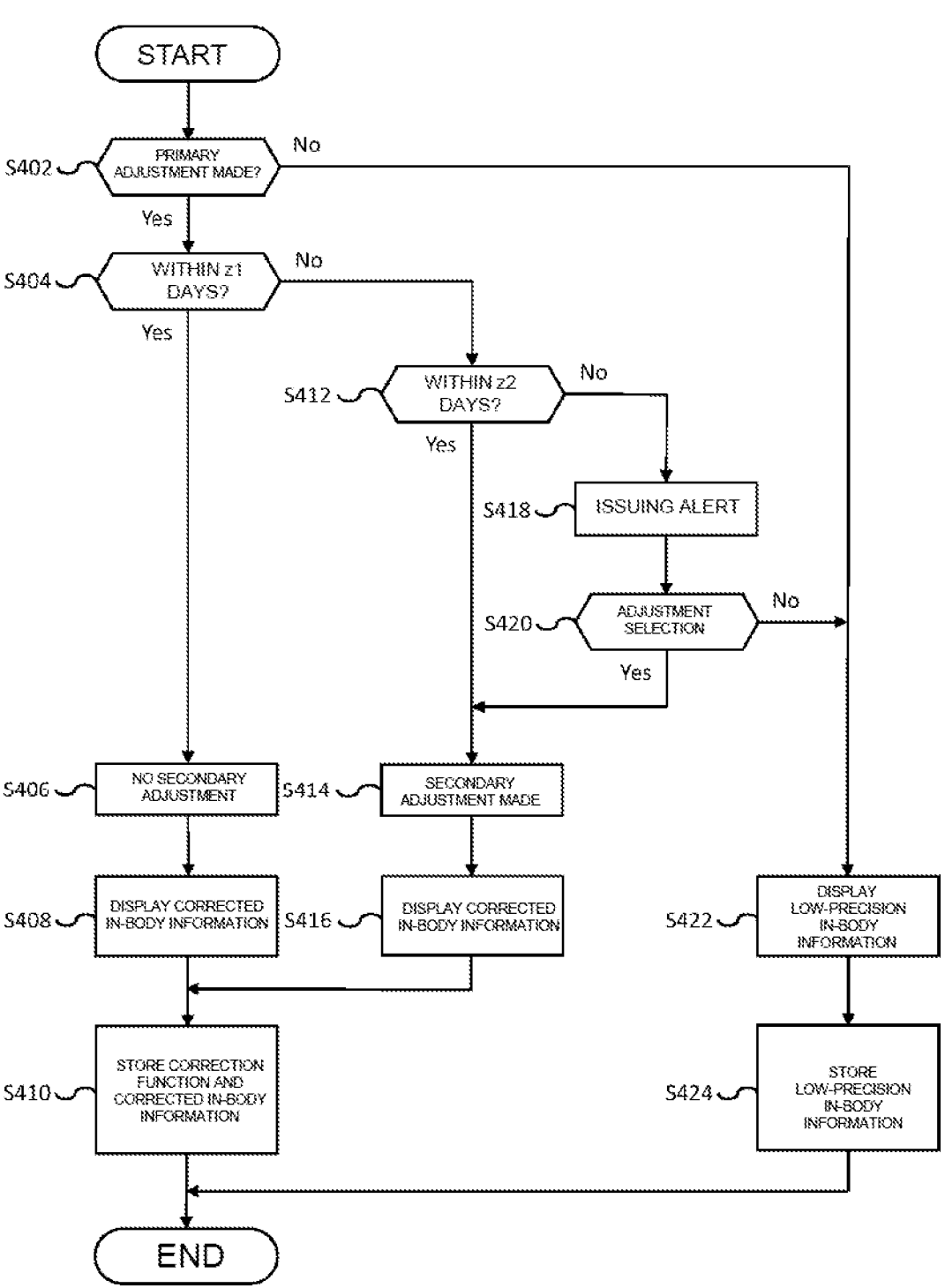
FIG. 7 shows a second flowchart showing operations of the simplified BIA body composition analyzer for determining the correction function according to the third embodiment.

FIG. 7 is a second flowchart showing the operation of a simplified BIA body composition analyzer 100 for determining a correction function according to a third embodiment of the present disclosure. The second flow in the third embodiment differs from the second flow in the first embodiment in that it is a flow for further secondary adjustment of the primarily adjusted high-precision reference value using the user's adjustment selection as an indicator in addition to the elapsed days. After the first flow is completed, the second flow in the third embodiment starts.

When the second flow starts, the correction unit 112 determines whether the primary adjustment has been made (Step S402) and the number of elapsed days (Step S404).

When it is determined that it is "primary adjustment made" and the number of elapsed days is "within z1 days" (Step S402: Yes, Step S404: Yes), the correction unit 112 determines a correction function based on the primarily adjusted high-precision reference value (Step S406) without performing secondary adjustment, and corrects the low-precision reference value by this correction function. The correction function is used to correct the low-precision reference value, and the output unit 106 displays the low-precision in-body information as the corrected low-precision reference value as the corrected in-body information (Step S408). Then, the memory unit 110 stores the correction function and the corrected in-body information (Step S410), and the flow ends.

That is, when the primary adjustment is made and the number of elapsed days is "within z1 days," the change in body composition between the high-precision measurement time and the low-precision measurement time is considered to be small, and the contribution of the high-precision reference value is determined to be high. In this case, the correction unit 112 does not perform the secondary adjustment.

On the other hand, when it is determined that it is "primary adjustment made" and the number of elapsed days is not "within z1 days" (Step S402: Yes, Step S404: No), the correction unit 112 determines the number of elapsed days again (Step S412).

If it is determined that the number of elapsed days is "within z2 days" (Step S412: Yes), or if the number of elapsed days is not "within z2 days" and an "issuing alert" to the user to urge measurement of a high-precision reference value (Step S418), but the user makes an "adjustment selection" (Step S420: Yes), the correction unit 112 determines the adjustment parameters $Y_{0-5}$, a, and b according to the degree of contribution, and adjusts the high-precision reference value by the secondary adjustment "(a×$Y_{0-5}$×high-precision reference value+b×low-precision reference value)/2" (Step S414). Then, the correction unit 112 corrects the low-precision reference value by a correction function based on the secondarily adjusted high-precision reference value, the output unit 106 displays the low-precision in-body information as the corrected low-precision reference value as the corrected in-body information (Step S416), the memory unit 110 stores the correction function and the corrected in-body information (Step S410), and the flow ends.

That is, when it is determined that a user to whom "issuing alert" has made an "adjustment selection" although it is "primary adjustment made" and the elapsed days are not "within z2 days," the correction unit 112 determines adjustment parameters $Y_{0-5}$, a, and b according to the contribution of the high-precision reference value, and adjusts the high-precision reference value according to the secondary adjustment "(a×$Y_{0-5}$×high-precision reference value+b×low-precision reference value)/2."

On the other hand, when it is determined that it is not "primary adjustment made" (Step S402: No), or when it is determined that it is "primary adjustment made" and the elapsed days are neither "within z1 days" nor "within z2 days" and the user did not make an "adjustment selection" although an "issuing alert" was made to the user to urge measurement of the high-precision reference value (Step S402: Yes, Step S404: No, Step S412: No, Step S418, Step S420: No), without the correction unit 112 correcting the low-precision reference value by the correction function, the output unit 106 displays the low-precision in-body information as the low-precision reference value (Step S422), and The output unit 106 displays the low-precision in-body information as the low-precision reference value (Step S422), and the memory unit 110 stores the low-precision in-body information as the low-precision reference value (Step S424), and the flow ends.

That is, when the number of elapsed days is neither "within z1 days" nor "within z2 days" in "with primary adjustment" and the user does not make an "adjustment selection," it is considered that the change in body composition between the high-precision measurement time and the low-precision measurement time is large and the contribution of the high-precision reference value is small. In this case, the correction unit 112 does not make any correction.

As described above, in the second flow in the third embodiment, the contribution of the high-precision reference value is evaluated using the elapsed days and the user's adjustment selection as indicators. Unlike the second flow in the first embodiment, when it is determined that a user to whom "issuing alert" has made an "adjustment selection" although the number of days has lapsed z2 days, the low-precision reference value is corrected by a correction function based on the secondarily adjusted high-precision reference value, and the low-precision in-body information as the corrected low-precision reference value is displayed as the corrected low-precision reference value, and the correction function and the corrected in-body information are stored. On the other hand, if it is determined that the user to whom "issuing alert" did not make an "adjustment selection," the low-precision in-body information as the low-precision reference value is displayed and the low-precision in-body information as the low-precision reference value is stored, without correcting the low-precision in-body information as the low-precision reference value with the correction function.

Thus, unlike the second flow in the first embodiment, the second flow in the third embodiment can determine the secondary adjustment based on the user's selection in addition to the number of elapsed days, thus providing a highly precise body measurement system and program tailored to individuals.

In addition, unlike the second flow in the first embodiment, the second flow in the third embodiment can provide a highly precise body measurement system and program tailored to individuals, because the alert can encourage the user to measure new high-precision reference values and motivate to increase the precision of the body measurement system.

In the second flow in the third embodiment, the timing for "issuing alert" is based on whether or not it is "within z2 days" from the high-precision measurement time as an indicator. This elapsed time "within z2 days" can be changed depending on the measurement method of the high-precision reference value. For example, when measuring the high-precision reference value using a body composition measurement (estimation) method with high measurement precision of in-body information, such as DXA, z2 may be set to a relatively long number of day since it is not a measurement method that can be measured frequently. On the other hand, when measuring the high-precision reference value using a high-precision BIA body composition method such as a multi-frequency and multi-electrode BIA body composition analyzer, z2 may be set to a relatively short number of days because it is a measurement method that can be measured more frequently than when measuring the high-precision reference value using DXA.

Figure 8:
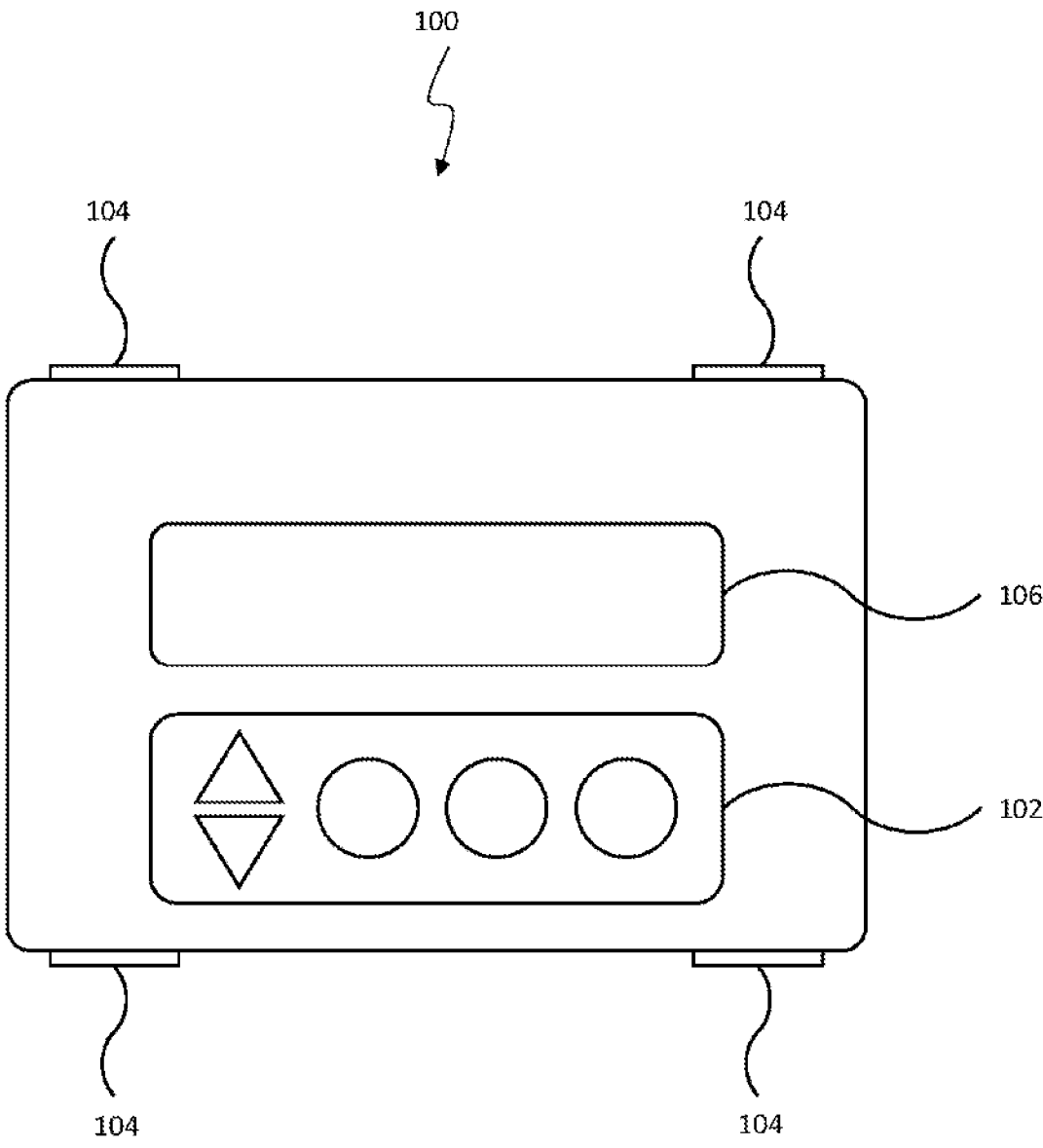
FIG. 8 shows a front view of a card-type simplified BIA body composition analyzer according to an embodiment.

As described above, in all of the first, second, and third embodiments of the present disclosure, the user can know highly precise in-body information even though the measurement is simple using the simplified BIA body composition analyzer 100. Here, the simplified BIA body composition analyzer 100 can be in any form, such as a flat type, a stand type, or a card type having an input unit 102, a low-precision measurement part 104, and an output part 106 as shown in FIG. 8, and the simple measurement can be any measurement that is less precise in measuring in-body information than the body composition measurement (estimation) method, such as a simple two-foot measurement or a simple two-hand measurement.

(Variant 1)

The flow in the above embodiment consists of the first flow and the second flow, but only the first flow without the second flow may be used. In this case, the adjustment parameters can be determined based only on the weight difference between the high-precision measurement time and the low-precision measurement time, and the high-precision reference value can be adjusted, and the correction function can be determined.

To explain referring to FIG. 3, in the first flow, the correction unit 112 determines a correction function based on the primarily adjusted high-precision reference value and the low-precision in-body information, and corrects the low-precision in-body information by this correction function. Then, this corrected low-precision in-body information is displayed as the corrected in-body information, and the correction function and the corrected in-body information are stored. This step can be provided as a step following each of step S110 and step S114.

The low-precision in-body information as the corrected low-precision reference value may be the average of the primarily adjusted high-precision reference value and the low-precision in-body information as the low-precision reference value corrected by the correction function.

(Variant 2)

Although the flow of the above embodiment consists of the first flow and the second flow, only the second flow without the first flow may be used. In this case, the adjustment parameters can be determined based only on the number of days elapsed between the high-precision measurement time and the low-precision measurement time, the high-precision reference value can be adjusted, and the correction function can be determined.

To explain referring to FIG. 4, when a user operates the simplified BIA body composition analyzer 100 to start the process of determining the correction function, the second flow starts. When the second flow starts, the user first goes through the steps of measuring the user's in-body information by the low-precision measurement unit 104 and the step of storing the low-precision in-body information in the storage unit 110. Then, instead of the step where the correction unit 112 determines whether the primary adjustment has made (Step S202), the correction unit 112 determines the presence or absence of the high-precision reference value stored in the memory unit 110. Then, the steps from step S204 to the end can be determined.

(Variant 3)

In the above embodiment, the correction unit 112 obtains the corrected in-body information by correcting the low-precision in-body information obtained by the low-precision measurement unit 104 with a correction function based on the high-precision reference value and the low-precision reference value, but the method of obtaining the corrected in-body information is not limited thereto.

The correction unit 112 may correct the algorithm used in the low-precision measurement unit 104 based on the high-precision reference value and the low-precision reference value. The low-precision measurement unit 104 obtains the corrected in-body information by inputting the measured values into the algorithm corrected by the correction unit 112.

For example, when the predetermined algorithm is a regression equation, the correction unit 112 corrects the predetermined regression equation, which outputs the low-precision in-body information when the measured values are input, to a regression equation that outputs the adjusted high-precision reference value when the measured values at the low-precision measurement time are input. The memory unit 110 stores the corrected regression equation, and in subsequent low-precision measurements, the low-precision measurement unit 104 obtains the corrected in-body information by inputting the measured values into the corrected regression equation. When a new high-precision reference value is obtained, the regression equation can be updated.

Thus, the correction unit 112 may correct the low-precision in-body information calculated by a predetermined algorithm in the low-precision measurement unit 104 by a correction function, as in the above embodiment, or it may correct the algorithm itself for calculating the low-precision in-body information from the measured values in the low-precision measurement unit 104, as in the above variation.

The correction unit 112 may also correct the predetermined algorithm itself based on the corrected in-body information and the low-precision in-body information calculated by the predetermined algorithm once the corrected in-body information is obtained. Once the algorithm has been corrected, the results of the subsequent low-precision measurements will be closer to the corrected in-body information. Therefore, once the algorithm is corrected, the difference between the corrected in-body information and the results of low-precision measurements becomes smaller, and a highly precise intra-body measurement system and program tailored to individuals can be provided.

(Variant 4)

In the above embodiment, the correction function was set in a single measurement by the low-precision measurement unit 104, but the correction function may be set after multiple measurements. For example, the measurement by the low-precision measurement unit 104 may be made twice, once on the first day and once on the second day, and the correction function may be set using the average of the low-precision in-body information as the low-precision reference value for the first day and the second day. In this case, the correction function may be set at the time of measurement by the low-precision measurement unit 104 on the second day. In this way, by setting the correction function after multiple measurements by the low-precision measurement unit 104, the correction function can be set using the low-precision in-body information that takes variability into account. Therefore, it is possible to provide a highly precise in-body measurement system and program tailored to individuals.

DESCRIPTION OF THE REFERENCES

100: Simplified BIA body composition analyzer
102: Input unit
104: Low-precision measurement unit
106: Output unit

24

108: Control unit
110: Memory unit
112: Correction unit
200A, 200B: Corrected in-body information
202B: Information related to the precision of the corrected in-body information

The invention claimed is:

1. An in-body measurement system, comprising:
a memory unit configured to store a first precision in-body information as information containing a plurality of types of reference values;
a low-precision measurement unit configured to obtain a second precision in-body information by inputting a measured value into a predetermined algorithm, where the second precision is lower than the first precision;
a correction unit configured to correct the predetermined algorithm or the second precision in-body information based on the first precision in-body information stored in the memory unit and a parameter corresponding to one type of reference value of the plurality of types of reference values; and
an output unit, comprising a display, configured to display a corrected in-body information value,
wherein the corrected in-body information value is the second precision in-body information obtained based on the corrected predetermined algorithm or the corrected second precision in-body information,
wherein the parameter is based on the difference between a body weight when the first precision in-body information is measured and a body weight when the second precision in-body information is measured,
wherein the parameter is different based on the corresponding type of reference value, and
wherein the display is configured to display the corrected in-body information in a manner visually distinguishable from the second precision in-body information.

2. The in-body measurement system according to claim 1, wherein the parameter is further based on a contribution of a reference value in the plurality of types of reference values that corresponds to the second precision in-body information.

3. The in-body measurement system according to claim 2, wherein the parameter is further based on a period of time between measuring the first precision in-body information and measuring the second precision in-body information.

4. The in-body measurement system according to claim 3, wherein the parameter is further based on a difference between the corresponding type of reference value of the plurality of types of reference values and the second precision in-body information.

5. The in-body measurement system according to claim 1, wherein the parameter is further based on a period of time between measuring the first precision in-body information and measuring the second precision in-body information.

6. The in-body measurement system according to claim 5, wherein the parameter is further based on a difference between the corresponding type of reference value of the plurality of types of reference values and the second precision in-body information.

7. The in-body measurement system according to claim 1, wherein the parameter is further based on a difference between the corresponding type of reference value of the plurality of types of reference values and the second precision in-body information.

8. The in-body measurement system according to claim 1, wherein the parameter is further based on a user's choice.

9. The in-body measurement system according to claim 1, wherein the memory unit is configured to store the corrected algorithm or a correction function for correcting the second precision in-body information and the corrected in-body information.

10. The in-body measurement system according to claim 1, further comprising an input unit configured to receive the first precision in-body information as an input.

11. The in-body measurement system according to claim 1, wherein the display is configured to display information related to a precision of the corrected in-body information based on the parameter.

12. The in-body measurement system according to claim 1, wherein the display is configured to display an alert based on a period of time between measuring the first precision in-body information and measuring the second precision in-body information.

13. The in-body measurement system according to claim 1, wherein the correction unit is configured to correct the predetermined algorithm or the second precision in-body information further based on a parameter corresponding to the corrected in-body information value.

14. A computer-readable non-transitory storage medium comprising a program for causing a computer to function as:

a memory unit configured to store a first precision in-body information as information containing a plurality of types of reference values;

a low-precision measurement unit configured to obtain a second precision in-body information by inputting a measured value into a predetermined algorithm, where the second precision is lower than the first precision;

a correction unit configured to correct the predetermined algorithm or the second precision in-body information based on the first precision in-body information stored in the memory unit and a parameter corresponding to one type of reference value of the plurality of types of reference values; and an output unit, comprising a display, configured to display a corrected in-body information value, wherein the corrected in-body information value is the second precision in-body information obtained based on the corrected predetermined algorithm or the corrected second precision in-body information, wherein the parameter is based on the difference between a body weight when the first precision in-body information is measured and a body weight when the second precision in-body information is measured, wherein the parameter is different based on the corresponding type of reference value, and wherein the display is configured to display the corrected in-body information in a manner visually distinguishable from the second precision in-body information.

* * * * *